United States Patent [19]

Jegers et al.

[11] Patent Number: 4,726,377
[45] Date of Patent: Feb. 23, 1988

[54] MODULAR CONTROL FOR TANNING BEDS

[76] Inventors: Viktor J. Jegers, 10101 Yukon Ave. South, Bloomington, Minn. 55438; Joseph E. Supplee, 3109 Golden Valley Rd., Golden Valley, Minn. 55422

[21] Appl. No.: 792,124

[22] Filed: Oct. 28, 1985

Related U.S. Application Data

[63] Continuation of Ser. No. 729,958, May 2, 1985.

[51] Int. Cl.⁴ .............................................. A61N 5/06
[52] U.S. Cl. .................................................... 128/376
[58] Field of Search .................. 128/376, 395, 396; 315/360; 361/331, 332, 333, 334, 392, 393, 394

[56] References Cited

U.S. PATENT DOCUMENTS

| | | | |
|---|---|---|---|
| 2,567,740 | 9/1951 | Smith | 361/334 X |
| 2,788,470 | 4/1957 | Giel et al. | 361/394 |
| 3,483,543 | 12/1969 | Flanagan | 361/394 |
| 4,283,661 | 8/1981 | Doty | 315/360 |

*Primary Examiner*—Anton O. Oechsle
*Attorney, Agent, or Firm*—Palmatier & Sjoquist

[57] ABSTRACT

A modular timer assembly for controlling tanning beds and alike including a power supply module and a plurality of removably attached timer modules affixed between end panels; the timer modules using reduced voltage current to control the external tanning beds; and an extendable means supplying line voltage and reduced voltage current to each module.

17 Claims, 9 Drawing Figures

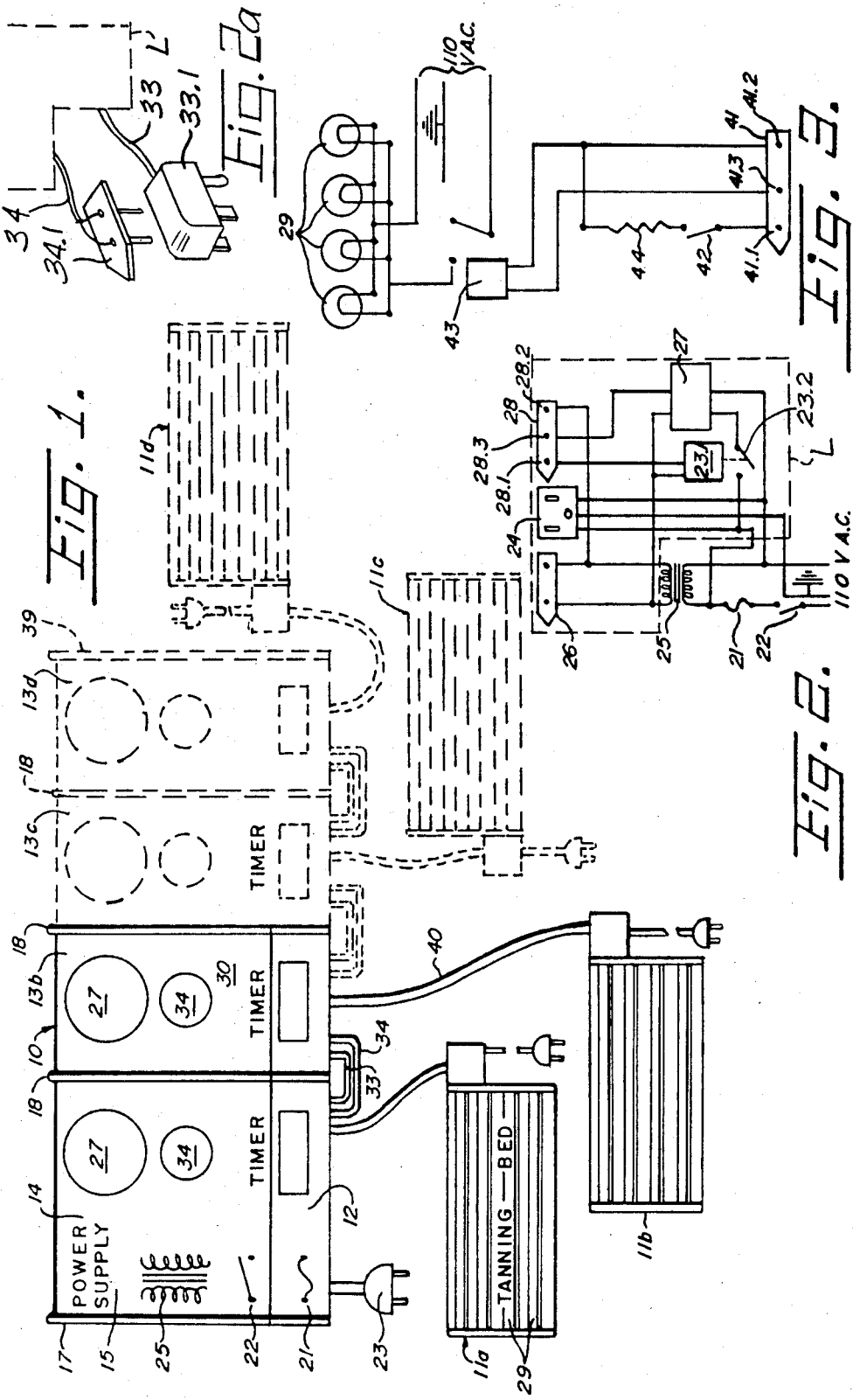

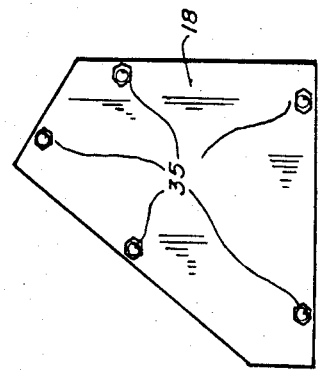
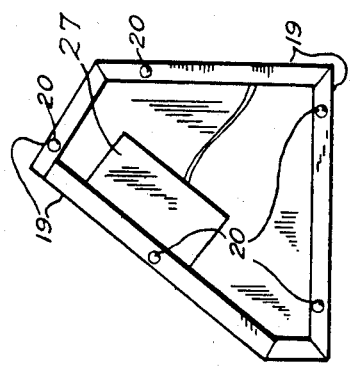
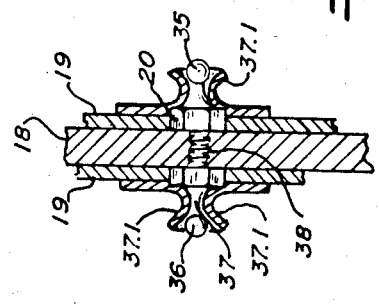
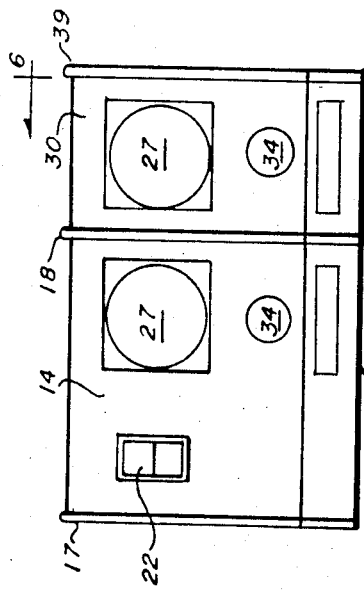
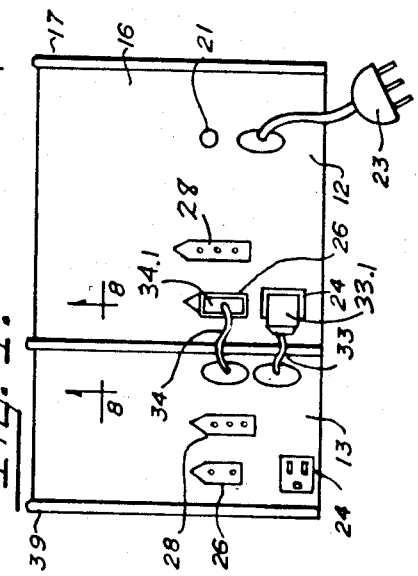

MODULAR CONTROL FOR TANNING BEDS

This is a continuation of U.S. patent application Ser. No. 729,958, filed on May 2, 1985.

BACKGROUND OF THE INVENTION

The invention relates to modular timer for remotely controlling multiple tanning beds. Timing devices, typically, have been designed to control a fixed number of electrical devices. Typically, the timer controls either one or a fixed number of tanning beds.

The currently popular tanning salons have a reception area where the customers enter and multiple private booths with tanning beds. The tanning booths are usually some distance from the reception area for convenience of the salon operator and to provide privacy in the individual tanning booths.

It is advantageous for the salon operator to control the time the tanning lights can be energized on each tanning bed assuring the customer receives the maximum tanning action while avoiding unnecessary risk of burning from overexposure to the tanning lamps. Additionally, by controlling the time the customer spends in the tanning booth, the salon can increase its profits.

When using the single booth timers, the operator purchases a complete timer unit for each of the tanning booths currently operating. This practice wastefully duplicates some functions in each of the timers. Also, the multiple single unit timers tend to be larger and waste counter space even when efficiently arranged. Each timer must each be connected to a source of electrical power which often leads to numerous tangled electrical cords leading to a limited number of electrical outlets.

Multiple booth timer control units contained in a single cabinet are available. The multiple control units require the salon operator to purchase the larger timer assembly to control only one tanning booth. This practice is both wasteful of counter space and uneconomical.

The multiple booth control units additionally usually cannot have timers added in the field requiring the timer and therefore the tanning booth it controls be taken out of service when additional timers are added. More importantly, when one timer requires repairs the entire timer assembly becomes unusable while the one timer is repaired.

Some single unit and multiple unit timers use line voltage (110 Volts A.C.) to control the remote tanning beds. When line voltage is used as such, the wiring must be done according to the prevailing Electrical Code and often requires inspection before the additional units can be put into service adding cost each time tanning booths are added to the salon.

SUMMARY OF THE INVENTION

An object of the invention is to provide an attractive, modular expandable tanning booth timer where additional timer modules can be easily and readily added when additional tanning beds are added to the salon.

Another object of the invention is to provide a modular controller using low voltages to control the remote tanning beds.

A feature of the invention is a modular timer assembly where a single power supply is adapted to provide the electrical current to a variable number of timer modules controlling the tanning beds. The power supply and timer modules are constructed in modular cases facilitating addition or replacement of the modules.

The power supply module contains a step down transformer supplying a reduced voltage current to the timers. A power switch and a fuse are affixed to the power supply case. The timer and timer reset controls are affixed to the front face of the power supply case integrating the first timer into the power supply module.

End panels are affixed to the open ends of the power supply case. The end panel adjacent the power supply is permanently attached to the power supply case and has its base flush with the base of the power supply case and extends outward past the remaining four edges of the power supply case.

At the timer end of the power supply case a similarly shaped end panel is removably attached. The removable end panel is attached using five ball studs extending into five spring loaded sockets within the module case.

The rear panel of the power supply case has a power supply connector for connection into a 110 volt A.C. line current. Sockets are provided for supplying both 110 volt and reduced voltage to the timer modules.

Each timer module contains a resettable timer for a tanning booth and the associated timer reset button and total hour meter. On the rear panel of each timer module are connection plugs supplying line voltage and reduced voltage to the timer module and line voltage and reduced voltage sockets for supplying current to an adjacent timer module. A three prong socket for receiving the tanning bed controller cord is also provided.

A tanning bed controller is attached to each tanning bed. The tanning bed controller has a normally open start switch actuated by movement of the tanning lamp assembly controlling current supplied to the timer motor. When energized, the timer also actuates a relay in the tanning bed controller supplying current to the tanning bed lamps.

The divider panels are a continuous panel covering the end of each module and separating the adjacent modules preventing an operator from exposing himself to the multiple current carrying terminals in several modules.

A divider panel is placed between two modules. The divider panel has dimensions to fit between and adjacent the modules having its base flush with the module base and extend outwardly past the remaining edges of the modules separating the modules.

The divider panel has five male ball studs attached on each of its surfaces extending into and releasably retained by the five female spring loaded sockets on the ends of the modules. The ball studs and sockets cooperate to attach each module to a divider panel and each divider panel to its two adjacent modules thereby connecting the modules together.

In use the power supply module is installed by placing it and a suitable number of timer modules on a convenient counter top. The timer modules line voltage and reduced voltage cords are then connected to the sockets in the adjacent sockets. The tanning booths using the low voltage lines control cords.

The removable end panel can be readily removed by moving it away from its end releasing the ball studs from their sockets. Likewise, a divider panel can be readily installed by placing it adjacent the timer case and urging its ball studs into the sockets in the power supply case.

When additional tanning booths are to be controlled, additional timer modules are added by first removing the timer module end panel and attaching a divider panel. The additional timer module is attached to the divider panel extending the timer assembly.

The additional timer module is placed adjacent the divider panel and the ball studs of the dividing panel urged into the mating sockets of the timer case. When the necessary number of timer modules have been so installed the original timer end panel is replaced on the far end of the modules.

Each timer panel so installed is electrically connected simply by inserting the low voltage and 110 volt power cords into the polarized sockets of the adjacent module. The added timer modules can then be connected to their respective tanning booths with the tanning bed control cord.

Thus the installation of a number of timers to control a number of tanning booths can readily be done in the tanning salon and requiring minimal skill.

In use low voltage current switched by the start switch energizes the timer and the relay controlling the tanning lamps. The lamps turn on when the customer reclined in the tanning bed moves the lamp assembly into its operating position closing the start switch and starting the timer to actuate the tanning lamps. After the preset time expires, the timer turns off the tanning lamps.

The principal advantage of the invention is it provides a modular expandable tanning booth timer where additional timer modules can be easily and readily added when additional tanning booths are added to the salon.

Another advantage of the invention is that it provides a modular controller using low voltages to remotely control a tanning booth.

BRIEF DESCRIPTION OF THE DRAWINGS

FIG. 1 is an overall diagrammatic view showing the modular timer assembly and tanning beds, and showing in dotted lines, additional timer modules for tanning beds.

FIG. 2 is an electrical schematic diagram of the circuit of the master controller.

FIG. 2a is a schematic diagram of the circuit of each expansion module.

FIG. 3 is an electrical schematic diagram of circuit of one tanning bed.

FIG. 4 is a front elevational view of the modular timer assembly with one timer module attached.

FIG. 5 is a rear elevation of the timer assembly with one timer module attached.

FIG. 6 is an end view of one module taken approximately at 6—6 of FIG. 4.

FIG. 7 is an elevational view of one divider panel.

FIG. 8 is an enlarged detailed cross sectional view of the ball stud connectors taken approximately at 8—8 of FIG. 5.

DETAILED SPECIFICATIONS

FIG. 1 diagrammatically shows the timer assembly 10 and a plurality of connected tanning beds 11a–11d. Timer assembly 10 has a power supply module 12 and one or more expansion modules 13b–13d. The power supply module 12 has an elongate metallic case 14 having a rearwardly sloping front face 15 and a vertical rear face 16. The terminal end panel 17 is attached to one side of the power supply case 14. A divider panel 18 is removably attached to the other end of the power supply case 14. The power supply module case 14 has perpendicular connector tabs or flanges 19 on its each end with stud sockets 20 affixed on the interior of the connector tabs to provide a quick disconnect snap on connection for the end and divider panels 17, 18.

The power supply module 12 also contains the electrical power supply for supplying line voltage (110 V) current and reduced voltage (24 V.) current to each timer assembly as shown schematically in FIG. 2. Electrical power supply has a power switch 22 for interrupting the current supply and a fuse 21.

Each expansion module 13b–13d is contained in a timer case 30 having a rectangular base and a rearwardly sloping front face 18. Each timer case 30 has end dimensions identical to the power supply module 12. Attached to the front face 18 is the timer 27 and its reset switch 34. Each timer case 30 has perpendicular end connector tabs or flanges 19 on its each end with stud sockets 20 affixed on the interior of the connector tabs 19, for connecting the end on divider panels 18, 39.

The line voltage is supplied in module 12 from plug 23 and through switch 22 and fuse 21 to transformer 25, and to timer 27, through contacts 23.2 of relay 23.1 and to rear mounted external socket 24 for supply to the additional timer modules 13. In timer 27, line voltage is used to operate a timer motor which opens control switches for the control of the related tanning bed.

The low voltage side of transformer 25 supplies 24 volt current for operating relay 23.1 and relay 43 at the tanning bed. A rear mounted external socket 28 on the case 14 has three sockets for a three prong plug 41 on the cord 40 which connects the module 12 to the tanning bed 11a. The socket 28 has connector sockets or terminals 28.1, 28.2 and 28.3. which fit with plug prongs or terminals 41.1, 41.2 and 41.3 respectively. One side of relay 43 is connected through connector terminals 41.2, 28.2 to one side of the low voltage power supply; and the other side of relay 43 is connected through terminals 41.3 and 28.3 and through the control switching of timer 27 to the other side of the low voltage power supply.

One side of relay 23.1 is connected directly to one side of the low voltage power supply; and the other side of relay 23.1 is connected through terminals 28.1, 41.1 and through start or control switch 42 at the tanning bed, and through terminals 41.2 and 28.2 to the other side of the low voltage power supply.

Another two terminal socket 26 is mounted on the rear of case 14 to supply low voltage power to the next expansion module.

In each of the expansion modules 13, especially modules 13b–13d, etc., the portion of the circuit of FIG. 2 and enclosed in the dotted line L is repeated. A line voltage cord 33 and plug 33.1 on the expansion module connects to the socket 24 of the adjacent module. A reduced voltage (24 volt) cord 34 and plug 34.1 on the expansion module connects to the socket 26 of the adjacent module. The corresponding tanning bed is connected to the module by cord 40 and plug 41 which connects to the socket 28 of the module.

At the tanning bed, the normally open sensor switch 42 senses the operational position of the tanning lights when the tanning lights are in operational position, the switch 42 is closed.

The timer 27 is preset for use of the tanning bed, and ready to start. When the tanning lights are moved to operational position, the switch 42 is closed to energize relay 23.1, thus closing the contacts 23.2 and applying power to the timer motor. After the preset time has elapsed, the timer opens the circuit for relay 43 which opens to turn the tanning lights off.

A divider panel 18 fits between the power supply case 14 and the case 30 of the first expansion module 13b and between each successive expansion modules 13. The divider panel 18 has dimensions to abut the end connector tabs 19 of the power supply case 14 of timer module case 30 so as a respective bases are flush and the divider panel 18 extends outwardly at the other sides of the module.

The divider panel 18 is constructed of a suitable rigid material, and is preferably constructed of one-eighth inch thick aluminum restricting operator access to the interior of the timer modules 13.

A plurality, preferably 5, ball stud 35 extend outwardly from each side of each divider panel 18. The ball studs 35 are located on a divider panel 18 so as to mate with the stud sockets 20 on the end connector tabs 19 of the adjacent cases 14 and 30. Ball studs 35 may be attached by any suitable means and are preferably attached using a threaded bolt 38 passing through the divider panel 18 and retaining each ball stud 35.

The ball studs 35 have a round head 36 and a reduced diameter neck 37. The ball stud head 36 passes into the stud socket 20 and is retained therein by the tension of the socket springs 37.1 on the interior of the connector tabs 19.

A removable end panel 39 is attached to the end of the timer assembly opposite the terminating end panel 17. The end panel 39 has identical dimensions to the divider panel 18 and is likewise preferably constructed from continuous sheet of one-eighth inch thick aluminum. The end panel 39 has a plurality, preferably 5, ball studs 35 extending from its one side located to mate with the stud socket 20 in the last timer module case 30.

In its use the power supply module 12 and the appropriate number of timer modules 13 are assembled. The modules are assembled by removing the end panel 39 from the power supply module 12. A first divider panel 18 is then placed adjacent the power supply module 12 and its ball studs 35 are urged into the mating sockets 20 on the end tab 19 of the power supply module 12.

In assembly, the ball studs 35 are urged into the stud sockets 20. The ball stud head 36 moving the socket springs 37.1 aside allowing the ball stud head 36 to pass between the socket springs 37.1 and disposing the reduced diameter neck 37 between the socket springs 37.1 where the ball stud 35 is retained by the tension of the socket spring 37.1 against the ball stud head 36.

The first timer module 13b is placed adjacent the first divider panel 18 and the ball studs 35 of the divider panel 18 are urged into the sockets 20 in the end tabs 19 of a timer module case 30 where the ball stud heads 36 are retained against the tension of the socket springs 37.1

Additional timer modules 13c, 13d may be added when needed. With the proper number of timer modules 13 attached adjacent the power supply module 12 the end panel 39 is attached to the end of the last timer module 13 by placing it adjacent and urging the ball studs 35 into the stud sockets 20 in the connector tabs 19 in the timer case 30.

The first timer module 13b is electrically connected from power supply module 12 by connecting its line voltage cord 33 into the line voltage socket 24 of the power supply module 12. The reduced voltage cord 34 of the timer module 13b is then plugged into the reduced voltage socket 26 of the power supply module 12.

Each successive timer module 13 is similarly connected placing the plug of the line voltage cord 33 into the adjacent line voltage socket 24 and the plug of the reduced voltage cord 34 into the adjacent reduced voltage socket 26. Timer assembly is thus assembled and is prepared for connection through the tanning bed connector 41 to the tanning bed 11.

The tanning beds 11 are connected through the tanning bed control cord 40 which terminates three connector polarized plug 41 adapted to fit into the bed connector 28 on the rear face 16 of the power supply module 12 or the rear face of a timer module 13.

The timer assembly 10 may now be connected using the power supply cord 23 to a source of line current and turned on using the power switch 22 ready for use.

In use the timer 27 is set for the appropriate tanning time for the client. The client retires to a distant tanning booth where he prepares for the tanning session. After the client is reclined in the tanning bed 11 the lamp assembly is moved into its operational position thereby closing the start switch 42, schematically shown in FIG. 3, energizing the timer relay 23.1 and starting the timer 27. As the timer 27 operates it energizes the lamp relay 43 starting the tanning lamps 29.

After the time preset on the timer 27, timer circuit opens de-energizing the lamp relay 43 and the tanning lamps 29 turn off. Additionally, during the tanning session should the client move the tanning lamps 29 from their operative position the start switch 42 is opened de-energizing and stopping the timer 27. The client may then return the tanning lamps 29 to their operative position closing the start switch 42, restarting the timer 27, and continuing his tanning session.

When the salon operator installs additional tanning beds, additional timer modules 13 are added to control the additional beds by removing the terminal end panel 39 and installing additional divider panels 18 and timer modules 13 and replacing the terminal end panel.

The added timer modules 13 are electrically connected by inserting their line voltage cord 33 into the adjacent line voltage outlet 24 and the reduced voltage cord 34 into the adjacent reduced voltage outlet 26. The plug 41 on the cord 40 of the additional tanning beds 11 is inserted into the bed connector 28 completing the installation.

If one of the timer modules 13 requires repairs, the one timer module 13 can easily be removed and serviced without effecting the operation of the remaining timer modules 13. The inoperative timer module 13 is removed by disconnecting the line voltage cord 33 and the reduced voltage cords 34 from the inoperative timer. Once electrically disconnected, the timer module 13 can be removed from the timer assembly 10 by applying force to move the adjacent divider panels 18 from the ends of the timer module 13. The movement will withdraw the ball studs 35 from the stud sockets 20 releasing the ball studs 35 so the inoperative timer module 13 can be removed for service. After the inoperative timer 13 is removed, the timer assembly 10 is reassembled without the inoperative timer module 13 remaining serviceable with one fewer timer module 13.

The present invention may be embodied in other specific forms without departing from the spirit or central attributes thereof, it is therefore desired that the present embodiment be considered in all respects as illustrative and not restrictive, reference being made to That which is claimed is:

1. A modular timer assembly having a power supply module and at least one timer module for controlling a plurality of tanning beds comprising, an extendable electrical control means having a line current source and a plurality of electrical outlets, each outlet cooperatively controlling the lights of one tanning bed, each module having a modular case confining the electrical control means, each modular case having one electrical outlet for timing one tanning bed having divider panels spanning the interspace between adjacent modular cases, each divider panel and modular case having confronting attachment faces, the attachment faces further having quick disconnect plug and socket connectors removably retaining the divider panels in the interspaces between the modular cases.

2. The modular timer assembly according to claim 1 and the electrical control means further comprising a transformer providing reduced voltage output current to each outlet.

3. The modular timer assembly according to claim 2 and the reduced voltage output current is twenty-four volts.

4. The modular timer assembly according to claim 1 and the plug and socket connectors are ball stud connectors.

5. The modular timer assembly according to claim 4 and the plug ball stud connectors are affixed to the panel attachment faces and the socket ball stud connectors sockets are affixed to the attachment faces of the modular cases.

6. The modular timer assembly according to claim 5 and there are five ball stud connectors on each panel attachment face.

7. A modular timer assembly having a power supply module and at least one timer module for controlling a plurality of therapeutic units comprising, an extendable electrical control means having a line current source and a plurality of electrical outlets, each outlet cooperatively controlling the operation of one therapeutic unit, each module having a modular case confining the electrical control means, each modular case having one electrical outlet for timing one therapeutic unit having divider panels spinning the interspace between adjacent modular cases, each divider panel and modular case having confronting attachment faces, the attachment faces further having quick disconnect plug and socket connectors removably retaining the divider panels in the interspaces between the modular cases.

8. The modular timer assembly according to claim 7 and the electrical control means further comprising a transformer providing reduced voltage output current to each outlet.

9. The modular timer assembly according to claim 8 and the reduced voltage output current is twenty-four volts.

10. The modular timer assembly according to claim 7 and the plug and socket connectors are ball stud connectors.

11. The modular timer assembly according to claim 10 and the plug ball stud connectors are affixed to the panel attachment faces and the socket ball stud connectors sockets are affixed to the attachment faces of the modular cases.

12. The modular timer assembly according to claim 11 and there are five ball stud connectors on each attachment face.

13. A modular timer assembly for controlling a plurality of therapeutic units each with an operating mechanism having a power supply module and at least one timer module comprising, an elongate power supply module case, closed at one end, having a current supply means providing a switchable source of current at line voltage and a reduced voltage;

each timer module having an elongate timer module case fitting adjacently spaced from the power supply case end and having a timer therein, the timer electronically communicating with the current supply means, and further having an external start switch, the start switch being operable to start and stop the time, and having means connecting the operating mechanism of therapeutic unit so as the operating mechanism is energized concurrently with the timer;

at least one divider panel fitting between two modules abutting and covering the respective ends thereof;

a cooperative connection means on the ends of the cases and the sides of the panels releasably retaining the respective case and confronting the respective panel side linearly aligning the adjacent modules and connected through the panel retained therebetween;

a terminal end panel dimensioned to abut and cover the one end of the one timer module most remote from the power supply module.

14. The modular timer assembly is claim 13, with a plurality of timer modules and having the power supply module and the first timer module both contained within an elongate power supply module case.

15. The modular timer assembly in claim 13 and the cooperative connection means are cooperating male and female ball stud connectors.

16. The modular timer assembly according to claim 15 and there are five ball stud connectors on each side of each divider panel.

17. The modular timer assembly according to claim 13 and the male ball stud connectors are affixed to the panel sides and the female ball stud connectors sockets are affixed to the ends of the modular cases.

* * * * *

UNITED STATES PATENT AND TRADEMARK OFFICE
CERTIFICATE OF CORRECTION

PATENT NO.   : 4,726,377
DATED        : February 23, 1988
INVENTOR(S)  : Viktor J. Jegers, Joseph E. Supplee It is certified that error appears in the above-identified patent and that said Letters Patent is hereby corrected as shown below:

Column 7, line 49, delete "spinning" and replace it with --spanning--.

Signed and Sealed this

Fourteenth Day of February, 1989

Attest:

DONALD J. QUIGG

Attesting Officer

Commissioner of Patents and Trademarks